(12) United States Patent
Johnston

(10) Patent No.: US 10,091,991 B2
(45) Date of Patent: Oct. 9, 2018

(54) ANTIMICROBIAL FILMS

(71) Applicant: Greenway Pest Products, LLC, Corpus Christi, TX (US)

(72) Inventor: Brandon Johnston, Gilmer, TX (US)

(73) Assignee: Greenway Pest Products, LLC, Corpus Christi, TX (US)

( * ) Notice: Subject to any disclaimer, the term of this patent is extended or adjusted under 35 U.S.C. 154(b) by 158 days.

(21) Appl. No.: 14/841,169

(22) Filed: Aug. 31, 2015

(65) Prior Publication Data

US 2016/0150776 A1    Jun. 2, 2016

Related U.S. Application Data

(60) Provisional application No. 62/201,481, filed on Aug. 5, 2015, provisional application No. 62/123,842, filed on Dec. 1, 2014.

(51) Int. Cl.
*A01N 25/24* (2006.01)
*A01N 25/10* (2006.01)
*A01N 25/34* (2006.01)

(52) U.S. Cl.
CPC ............. *A01N 25/24* (2013.01); *A01N 25/10* (2013.01); *A01N 25/34* (2013.01)

(58) Field of Classification Search
CPC .................................................... A01N 25/24
See application file for complete search history.

(56) References Cited

U.S. PATENT DOCUMENTS

| 8,163,384 | B2 | 4/2012 | Hartman et al. | |
|---|---|---|---|---|
| 8,318,282 | B2 | 11/2012 | Ylitalo et al. | |
| 2007/0207335 | A1* | 9/2007 | Karandikar | B32B 15/01 428/560 |
| 2008/0131676 | A1* | 6/2008 | Becke | A61F 13/5146 428/216 |
| 2009/0035342 | A1* | 2/2009 | Karandikar | A01N 25/34 424/411 |
| 2010/0055157 | A1* | 3/2010 | Gunn | A61K 33/38 424/447 |
| 2010/0104791 | A1 | 4/2010 | Baudrion et al. | |
| 2014/0044766 | A1 | 2/2014 | Baudrion et al. | |
| 2014/0323578 | A1 | 10/2014 | Haddad et al. | |

* cited by examiner

*Primary Examiner* — Benjamin J Packard
(74) *Attorney, Agent, or Firm* — Gordon & Jacobson, P.C.

(57) ABSTRACT

Antimicrobial films are disclosed herein. The antimicrobial films are configured for application to surfaces, particularly to surfaces with which humans and animals come into contact. The antimicrobial films include a substrate layer and an antimicrobial layer. The substrate layer is generally a polymer, such as polyethylene. The antimicrobial layer is generally a composition of an antimicrobially-active ingredient dispersed in a dispersant. Typical dispersants include aqueous-based or solvent-based components (e.g., inks, primers, or varnishes). Antimicrobial films, as described herein, may be affixed to surfaces using an adhesive. Alternatively, the antimicrobial films may be applied to a surface using a heat-shrink process.

23 Claims, 2 Drawing Sheets

ANTIMICROBIAL FILMS

CROSS REFERENCE TO RELATED APPLICATIONS

This is a non-provisional of U.S. Provisional Patent Application Ser. Nos. 62/123,842, filed Dec. 1, 2014, and 62/201,481, filed Aug. 5, 2015, to which priority is claimed, and which are incorporated herein by reference in their entirety.

FIELD OF THE INVENTION

This application relates to the field of coatings and adhesives, and more particularly, relates to adhesive antimicrobial films.

BACKGROUND

Growth and accumulation of microbes on surfaces contributes to infection and illness of humans and animals that interact with those surfaces. Combatting such modalities of infection and illness is particularly important as antibiotic resistant strains of bacteria such as Methicillin Resistant *Staphylococcus Aureus* (MRSA) have emerged in recent decades. Surface-disposed bacteria also contribute to fouling and odor of surfaces, a problem less dire than the impact of bacteria growth on human and animal health, but one that must still be solved.

Generally, there are two ways to prevent or control microbes on surfaces—(1) disinfecting the surfaces once the microbes are established, or (2) modifying the surfaces to render then less hospitable to microbes in the first place. A problem with disinfection is that it must be performed on a continual and regular basis. Making the surfaces themselves antimicrobial is an attractive alternative or addition to regular disinfecting. One method of modifying a surface is to apply an antimicrobial coating to it. Ideally, such antimicrobial coatings should be: effective at preventing microbe growth and accumulation, easy to apply (and change periodically as the coating loses its efficacy), environmentally friendly and non-toxic to humans and animals, and aesthetically pleasing.

SUMMARY

Antimicrobial films are described herein. The antimicrobial films are configured for application to surfaces, particularly to surfaces with which humans and animals come into contact. According to certain embodiments, the antimicrobial films include a substrate layer and an antimicrobial layer. The substrate layer is generally a polymer, such as polyethylene. The antimicrobial layer is generally a composition of an antimicrobially-active ingredient dispersed in a dispersant. Typical dispersants include aqueous-based or solvent-based components (e.g., inks, primers, or varnishes) that are commonly used to print onto polymer films. Examples of suitable dispersants include acrylic pigmented or non-pigmented inks. One or more antimicrobial layers can be applied to the substrate using a printing technique, such as a roller film transfer technique.

Antimicrobial films, as described herein, may be affixed to surfaces using an adhesive. Generally, any adhesive (and adhesive/release backing combination) used in the tape and coating industry can be used to apply the antimicrobial films. Alternatively, the antimicrobial films may be applied to a surface using a heat-shrink process. The antimicrobial films may include other components, such as pest-deterring compounds, graphics layers including pigmented inks (for printing, bar codes, images etc.), texturing, and the like.

DESCRIPTION

Figure 1:
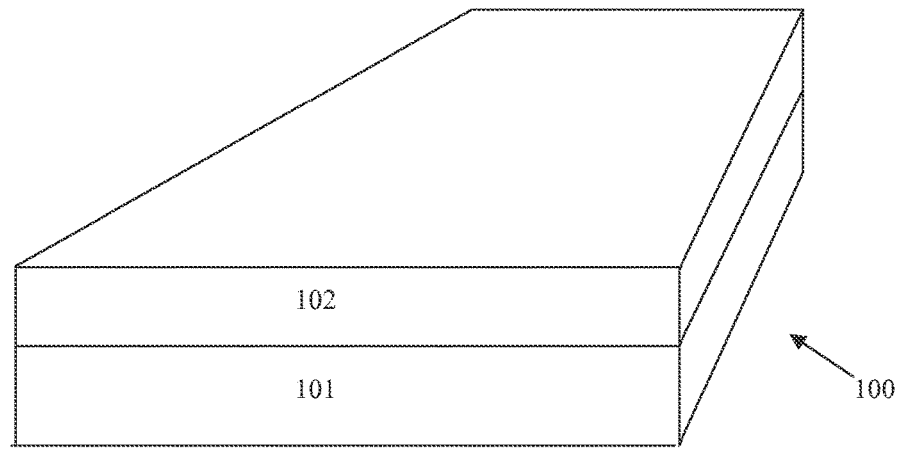
FIG. 1 illustrates an antimicrobial film.

As mentioned above, modifying a surface to render that surface inhospitable to microbes can help prevent the spread of infection and can help keep the surface clean and odor free. This disclosure describes antimicrobial films that can be applied to surfaces. FIG. 1 illustrates a simple embodiment of an antimicrobial film 100 having a substrate 101 and an antimicrobial layer 102. The substrate 101 is typically a polymer. Examples of suitable polymers films for substrates include polyolefin such as polyethylene or polypropylene, polyester, polyvinyl chloride, polystyrene, polyurethane, polybutadiene, and the like. A particularly suitable substrate material is linear low density polyethylene (LLDPE). The substrate may be any thickness (note that FIG. 1 is not drawn to scale), but generally, a flexible substrate that can be applied to surfaces is ideal. For example, the substrate 101 may be a polyethylene material having a thickness of about 0.5 to about 100 mil (1 mil=0.001 inches), about 1 to about 50 mil, or about 5 to about 15 mil. For many applications it is desirable that the substrate 101 be transparent and clear. According to certain embodiments, the polymer substrate is capable of bending around corners and other features of the surface to be treated.

The antimicrobial layer 102 includes an antimicrobially active ingredient dispersed in a dispersant. Examples of suitable antimicrobially active ingredients include metals such as copper and silver, titanium dioxide, organosilanes, triclosan, and ammonium-based compounds. Metals, such as silver and copper are particularly appropriate because of their high antimicrobial activity and their environmental friendliness. Such metals may be in the form of elemental particles (particularly nanoparticles) or as salts or organometallic compounds. One especially suitable antimicrobially active ingredient is a composition having a metal adsorbed or embedded within a zeolite carrier material. For example, AGION™ (Agion Technologies) features silver ions embedded within micron-sized zeolite materials. When ambient moisture or contact of the AGION activates the release of silver ions from the zeolite material. The silver ions act as a broad-spectrum antimicrobial.

Suitable dispersants for the antimicrobial layer 102 can include any material that can disperse the antimicrobially-active ingredient and that can secure a layer of the antimicrobially-active ingredient to the substrate 101. Particularly useful dispersants include solvent-based or aqueous-based inks and/or coatings that are commonly used to print onto polymer films. It is generally desirable to coat the entire surface of the substrate 101 with the antimicrobially-active ingredient. Therefore, the antimicrobially-active ingredient will typically not be dispersed only in an ink/coating that is used only to coat a portion of the substrate (for example, an ink used only to print graphics, such as lettering, images, bar codes, or the like). Instead, the antimicrobially-active ingredient should be dispersed in an ink/coating that is used to coat the entire surface (or nearly the entire surface) of the substrate 101. Examples of such appropriate ink/coatings include pigmented inks that may be used to coat the entire surface of the substrate 101. Other appropriate ink/coatings include pigmented or non-pigmented primer coatings, varnish coatings, and the like. Specific dispersants for the antimicrobial layer 102 include acrylic-based pigmented or non-pigmented top coats. The acrylic-based top coat may include additives, such as wax, to impart scratch resistance. For example, a non-pigmented acrylic top coat may include about 3% wax.

According to certain embodiments, the antimicrobially-active ingredient is dispersed into the dispersant at a concentration of 0.25% to about 5%. According to some embodiments, the antimicrobially-active ingredient is dispersed into the dispersant at a concentration of about 1% to about 3.5%.

The mixture of antimicrobially-active ingredient and dispersant can then be applied to the substrate 101 using any coating application or printing technique known in the art. Generally, such a technique is a printing (or film transfer) technique, such as Rotogravure printing or Meyer rod coating, whereby the mixture is transferred to substrate using rollers. According to certain embodiments, a roll of the substrate 101 is wound through the printing process, whereby a functional layer (antimicrobial layer 102) of the antimicrobially-active ingredient and dispersant is applied to the substrate 101. A process wherein a roll of the substrate is fed through the printing process is known as web printing. According to certain embodiments, the functionalized (printed) substrate is rerolled, yielding a roll of antimicrobial film 100—a process known as roll-to-roll processing.

The antimicrobial layer 102 can generally be any thickness. For example, it is typically about 1 to about 100 microns thick, or about 2 to about 50 microns thick, or about 5 to about 10 microns thick.

Figure 2:
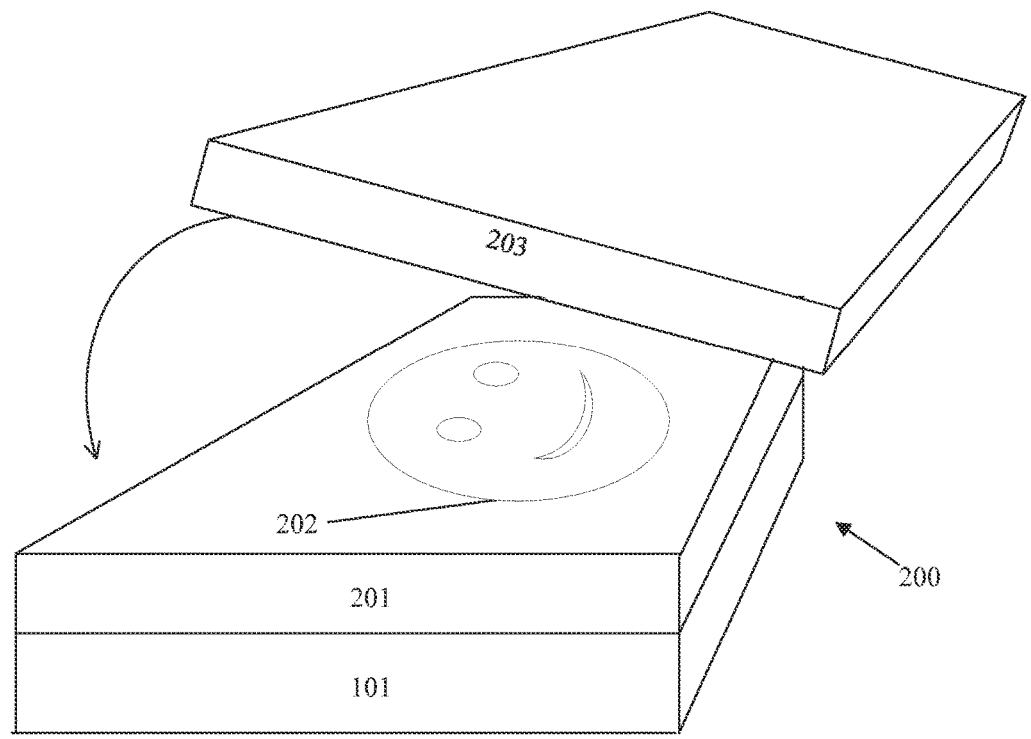
FIG. 2 illustrates an antimicrobial film having a graphics layer.

As mentioned above, it is typically preferable that the antimicrobially-active ingredient be disposed upon the entire surface of the substrate instead of only upon portions of the substrate. FIG. 2 illustrates a film 200 that includes two printed layers disposed on the substrate 101—a graphic layer 201, which includes an image 202, and a varnish layer 203 (shown removed, for clarity). In the film 200 it would be most appropriate that the varnish layer 203 be the antimicrobial layer. According to certain embodiments, the antimicrobially-active layer covers greater than 50% of the surface of the substrate. According to certain embodiments, the antimicrobially-active layer covers greater than 75% of the surface of the substrate. According to certain embodiments, the antimicrobially-active layer covers greater than 90% of the surface of the substrate. According to certain embodiments, the antimicrobially-active layer covers greater than 99% of the surface of the substrate.

Films such as those illustrated in FIGS. 1 and 2 can be applied to most any surface, particularly surfaces that humans or animals interact with. Examples include countertops, desks, all manner of keyboards and control panels, remote controls, push plates for doors, light switches, etc. Particularly suitable applications include medical, dental, cosmetology, tanning, and massage settings. For example, antimicrobial films can be incorporated into barrier tape (film) that is typically applied to surfaces such as chair arms, movable lights, and other surfaces during dental procedures, x-ray procedures, laboratory procedures, and the like. According to certain embodiments, the antimicrobial films described herein are capable of conforming to the shape of the surfaces to which they are applied. For example, the antimicrobial films can bend around corners and edges without cracking.

Films may also be applied to walls, within attics and basements, windows, crawl spaces, inside ducting and around HVAC components, essentially anywhere that is susceptible to bacteria, mold, or fungus growth. In such building applications, the films may include a pest-repelling agent in addition to an antimicrobially-active ingredient. Any pest-repelling agent can be used. Particular pest-repelling agents are described in co-owned patent application Ser. No. 14/810,956, filed, Jul. 28, 2015, the entire contents of which are incorporated herein by reference.

Figure 3:
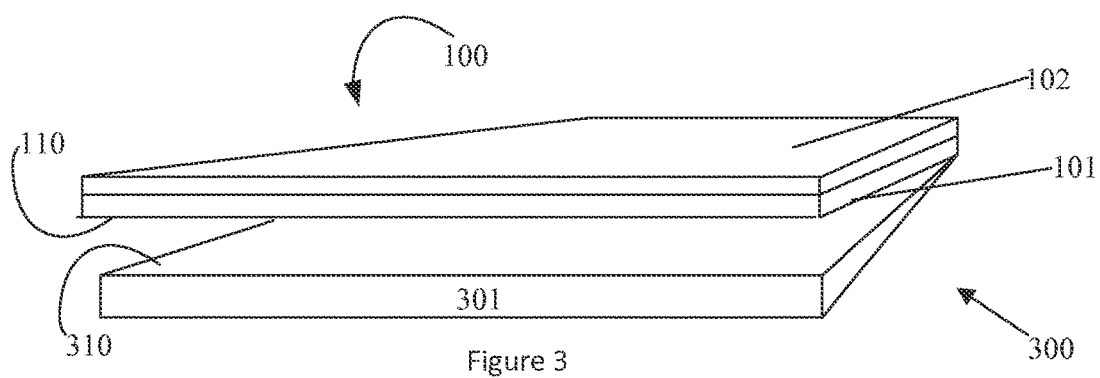
FIG. 3 illustrates a composite of an antimicrobial film disposed upon a release backing.

Antimicrobial films, as described herein, are typically applied to surfaces using an adhesive. Examples of suitable adhesives include silicones, rubbers, acrylics, and mixtures thereof. FIG. 3 illustrates a composite 300 having an antimicrobial film 100 (such as the one illustrated in FIG. 3) disposed on a release liner 301. The antimicrobial film 100 includes a substrate 101 and an antimicrobial layer 102. The antimicrobial film 100 may include other layers, as described above, such as graphic layers, primer layers, and the like. The release liner 301 is typically a sheet of material that serves as a carrier for the antimicrobial film 100. The release liner 301 is generally of a material such as cellulose (e.g., paper) or plastic. Release liners and adhesives are well known in the art and may be tailored depending on the specific application of the antimicrobial films described herein. The adhesive may be applied to one or both of surface 110 of the antimicrobial film 100 or surface 310 of the release liner 301.

According to certain embodiments, the antimicrobially-active ingredient can be applied to the bottom of the substrate as well as the top of the substrate. In other words, the antimicrobially-active ingredient can be applied to the same surface of the substrate as the adhesive. This embodiment has the advantage that when the film is applied to the surface, the antimicrobially-active ingredient can treat microbial contamination within the surface itself (e.g., mold, fungus, etc. that may be present within the surface material). Also, when the film is removed, a residue of the antimicrobially-active ingredient remains upon the surface (potentially, along with a residue of the adhesive) providing continuing antimicrobial treatment of the surface.

According to alternative embodiments, the antimicrobial film 100 may be heat shrunk or heat cured onto a surface. For example, the film may be applied directly onto a surface, smoothed to remove bubbles or air gaps between the film and the surface, and then exposed to heat (for example, using a heat gun or hair dryer) to form a stable bond between the film and the surface.

Composites 300 may generally be any shape or size, depending on their intended use. They may be formed into sheets, for example, or may be ribbons or spools which may, or may not, be configured within a dispenser.

An advantage of the film-based antimicrobial treatments described herein is that the films can be easily replace periodically as the efficacy of the film degrades. Such film replacement can be integrated into a regular maintenance schedule, for example.

Those of skill in the art will recognize that numerous modification and changes may be made to the exemplary designs and embodiments described herein and that the invention is limited only by the claims that follow and any equivalents thereof.

What is claimed is:

1. An antimicrobial film, comprising:
a polymer film substrate;
an antimicrobial coating disposed as a layer upon a first surface of the substrate and a second surface of the substrate, the antimicrobial coating comprising an antimicrobially-active ingredient and a dispersant, wherein the first surface and the second surface are on opposite sides of the substrate; and
an adhesive disposed upon the second surface of the substrate.

2. The antimicrobial film of claim 1, wherein the polymer substrate is selected from the group consisting of polyolefin, polyester, polyvinyl chloride, polystyrene, polyurethane, and polybutadiene.

3. The antimicrobial film of claim 1, wherein the polymer substrate is linear low density polyethylene.

4. The antimicrobial film of claim 1, wherein the antimicrobially-active ingredient is selected from the group consisting of metals, titanium dioxide, organosilanes, triclosan, and ammonium-based compounds.

5. The antimicrobial film of claim 4, wherein the antimicrobially-active ingredient comprises a metal selected from the group consisting of copper and silver.

6. The antimicrobial film of claim 5, wherein the antimicrobially-active ingredient comprises copper or silver ions adsorbed to a zeolite material.

7. The antimicrobial film of claim 1, wherein the dispersant is an ink, primer, or varnish.

8. The antimicrobial film of claim 1, wherein the concentration of antimicrobially-active ingredient is present in the dispersant is 0.5 weight percent to about 5 weight percent.

9. The antimicrobial film of claim 1, wherein the antimicrobial film is clear and transparent.

10. The antimicrobial film of claim 1, wherein the antimicrobial film is configured to adhere to a surface of an object when heat is applied to the film.

11. The antimicrobial film of claim 1, wherein the substrate is about 5 mil to about 15 mil in thickness.

12. The antimicrobial film of claim 1, wherein the antimicrobial layer is about 5 microns to about 10 microns thick.

13. A method of making an antimicrobial film, the method comprising:
dispersing an antimicrobially-active ingredient in a dispersant to form a mixture,
printing a coating of the mixture upon a first surface and a second surface of a substrate as a layer using a printing technique, wherein the substrate comprises a polymer film, wherein the first surface and the second surface are on opposite sides of the substrate; and
disposing an adhesive upon the second surface of the substrate.

14. The method of claim 13, wherein the dispersant is an acrylic polymer.

15. The method of claim 13, wherein the printing technique is a web printing technique.

16. A method of preventing microbial growth and accumulation on a surface, the method comprising:
applying an antimicrobial film to the surface, wherein the antimicrobial film comprises:
a polymer film substrate, and
an antimicrobial coating disposed as a layer upon a first surface of the substrate and a second surface of the substrate, the antimicrobial coating comprising an antimicrobially-active ingredient and a dispersant, wherein the first surface and the second surface are on opposite sides of the substrate, and
an adhesive disposed upon the second surface of the substrate.

17. The method of claim 16, wherein the substrate is linear low density polyethylene.

18. The method of claim 16, wherein the antimicrobially-active ingredient comprises a metal selected from the group consisting of copper and silver.

19. The antimicrobial film of claim 3, wherein the dispersant comprises acrylic.

20. The antimicrobial film of claim 19, wherein the coating further comprises wax.

21. An antimicrobial tape film, comprising:
a polymer film substrate;
an antimicrobial coating disposed as a layer upon a first surface of the substrate and a second surface of the substrate, the antimicrobial coating comprising an antimicrobially-active ingredient and a dispersant;
adhesive disposed on the second surface of the substrate; and
a release liner in contact with the adhesive, wherein the first surface and the second surface are on opposite sides of the substrate.

22. The antimicrobial tape film according to claim 21 wherein the dispersant comprises acrylic, and the polymer film substrate comprises linear low density polyethylene.

23. The antimicrobial tape film according to claim 22, arranged as a roll of tape.

* * * * *